US008987524B2

(12) United States Patent
Braun

(10) Patent No.: US 8,987,524 B2
(45) Date of Patent: Mar. 24, 2015

(54) PROCESS FOR THE MANUFACTURE OF SEVOFLURANE

(75) Inventor: Max Josef Braun, Wedemark (DE)

(73) Assignee: Solvay Fluor GmbH, Hannover (DE)

( * ) Notice: Subject to any disclaimer, the term of this patent is extended or adjusted under 35 U.S.C. 154(b) by 435 days.

(21) Appl. No.: 13/389,449

(22) PCT Filed: Aug. 10, 2010

(86) PCT No.: PCT/EP2010/061645
§ 371 (c)(1),
(2), (4) Date: Feb. 8, 2012

(87) PCT Pub. No.: WO2011/018466
PCT Pub. Date: Feb. 17, 2011

(65) Prior Publication Data
US 2012/0157708 A1    Jun. 21, 2012

(30) Foreign Application Priority Data

Aug. 10, 2009    (EP) ..................................... 09167529

(51) Int. Cl.
C07C 41/22    (2006.01)
C07C 51/367    (2006.01)
C07C 231/12    (2006.01)
C07C 67/31    (2006.01)

(52) U.S. Cl.
CPC ................. *C07C 41/22* (2013.01); *C07C 67/31* (2013.01)
USPC ............ 568/683; 560/180; 562/583; 564/160

(58) Field of Classification Search
None
See application file for complete search history.

(56) References Cited

U.S. PATENT DOCUMENTS

| | | | |
|---|---|---|---|
| 3,096,344 A * | 7/1963 | Case .............................. 549/511 |
| 3,911,024 A | 10/1975 | Croix |
| 3,956,381 A | 5/1976 | Krause |
| 4,228,300 A | 10/1980 | Lannert |
| 4,250,334 A | 2/1981 | Coon et al. |
| 5,705,710 A | 1/1998 | Baker et al. |
| 5,886,239 A | 3/1999 | Kudzma et al. |
| 5,969,193 A | 10/1999 | Terrell |
| 6,100,434 A | 8/2000 | Bieniarz et al. |
| 7,145,046 B2 | 12/2006 | Braun et al. |
| 8,013,182 B2 | 9/2011 | Yamamoto et al. |
| 2003/0144538 A1 | 7/2003 | Bartek et al. |
| 2009/0247791 A1 | 10/2009 | Pacheco et al. |

FOREIGN PATENT DOCUMENTS

| | | |
|---|---|---|
| DE | 2449899 A1 | 9/1975 |
| EP | 0792878 A2 | 9/1997 |
| EP | 0895991 A2 | 2/1999 |
| EP | 2039675 A1 | 3/2009 |
| GB | 1374054 A | 11/1974 |
| WO | WO 2004065340 A1 | 8/2004 |
| WO | WO 2009063783 A1 | 5/2009 |
| WO | WO 2009085247 A2 | 7/2009 |

OTHER PUBLICATIONS

Wang (Organic Reactions, vol. 34, 1985, pp. 319-400).*
Peters et al. (Journal of Chemical and Engineering Data, vol. 16, No. 3, 1071, pp. 376-377).*
Pryde, John, et al—"No. 385—New Derivatives of Methoxymalonic Acid", 1933, Journal of the Chemical Society (Resumed), pp. 1627-1628; 2 pgs.
Vida, Julius A., et al—"Analgesics. 2. Selected 5-Substituted 5-(1-Phenylethyl)barbituric Acids", 1974, J Medicinal Chemistry vol. 17, Issue No. 11, pp. 1194-1197, XP009142849; 4 pgs.
Kuwano, Ryoichi, et al—"Palladium-catalyzed benzylation of active methine compounds without additional base: Remarkable effect of 1,5-cyclooctadiene", 2004, Organic Letters, vol. 6, Issue No. 20, 30, pp. 3545-3547, XP009142778; 3 pgs.
Bogdanova, Aneta, et al—"Experimental and theoretical analysis of the photochemistry and thermal reactivity of ethyl diazomalonate and its diazirino isomer. The role of molecular geometry in the decomposition of diazocarbonyl compounds", 2004, Journal of the American Chemical Society, vol. 126, Issue No. 36, pp. 11293-11302; XP009142779; 10 pgs.
Ledon, H., et al—"No. 351—Reactivite des carbenes et carbenoides issus de la decomposition du diazomalonate de dimethyle", 1973, Bulletin de la société chimique de France, pp. 2065-2071; 6 pgs (includes abstract in English).
Zasosov, V.A., et al—"Synthesis of 4-(p-aminobenzenesulfamido)-5,6-dimethoxypyrimidine", 1972, Pharmaceutical Chemistry Journal, vol. 6, Issue No. 3, pp. 160-164, XP009019218; 5 pgs.
Crutchfield, M.M.—"Organic Builders: A Review of Worldwide Efforts to Find Organic Replacements for Detergent Phosphates", 1978, Journal of the American Oil Chemists' Society, vol. 55, Issue No. 1, pp. 58-65; XP009142725; 8 pgs.
Trost, Barry M., et al—"Geminal Dicarboxylates as Carbonyl Surrogates for Asymmetric Synthesis. Part II. Scope and Applications", 2001, Journal of the American Chemical Society, vol. 123, Issue No. 16, pp. 3687-3696; 10 pgs.
Godleski, Stephen A., et al—"Bis(allyl)di—chlorodipalladium", 2006. Encyclopedia of Reagents for Organic Synthesis, John Wiley & Sons, Ltd.; 51 pgs.

(Continued)

*Primary Examiner* — Rosalynd Keys

(57) ABSTRACT

A process for the manufacture of Sevoflurane $CF_3$—$CH(OCH_2F)$—$CF_3$ which comprises (a) manufacturing a substituted malonic acid derivative of formula (I): $R_1OOC$—$CH(OCH_2X)$—$COOR_2$ or of formula (II): $R_3HNOC$—$CH(OCH_2X)$—$CONHR_4$, wherein X is OH or a leaving group which can be substituted by nucleophilic substitution and wherein $R_1$, $R_2$ $R_3$, $R_4$, equal to or different from each other, are independently selected from the group consisting of H, an alkyl group having from 1 to 10 carbon atoms which is optionally substituted by at least one halogen atom, an aralkyl group, and an aryl group; and (b) further reacting said malonic acid derivative as intermediate for the manufacture of Sevoflurane $CF_3$—$CH(OCH_2F)$—$CF_3$.

24 Claims, No Drawings

(56) References Cited

OTHER PUBLICATIONS

Trost, Barry M., et al—"A Stereospecific Ruthenium-catalyzed Allylic Alkylation", 2002, Angewandte Chemie—International Edition, vol. 41, Issue No. 6, pp. 1059-1061; 3 pgs.

Hasek, W.R., et al—"The Chemistry of Sulfur Tetrafluoride. II. The Fluorination of Organic Carbonyl Compounds", 1960, Journal of the American Chemical Society, vol. 82, Issue No. 3, pp. 543-551; 9 pgs.

Dmowski, W., et al—Selective reactions of 1,1-cycloalkanedicarboxylic acids with SF4. A route to 1,1-bis(trifluoromethyl)cycloalkanes, 1-fluoroformyl-1-(trifluoromethyl)cycloalkanes and 1-(trifluoromethyl)-1-cycloalkanecarboxylic acids, 2000, Journal of Fluorine Chemistry, vol. 102, Issue No. 1-2, pp. 141-146, Elsevier; 6 pgs.

\* cited by examiner

PROCESS FOR THE MANUFACTURE OF SEVOFLURANE

CROSS-REFERENCE TO RELATED APPLICATIONS

This application is a U.S. national stage entry under 35 U.S.C. 371 of International Application No. PCT/EP2010/061645 filed Aug. 10, 2010, which claims priority to European Application No. 09167529.8 filed on Aug. 10, 2009, the whole content of this application being incorporated herein by reference for all purposes.

The present invention relates to a process for preparing Sevoflurane, $CF_3$—$CH(OCH_2F)$—$CF_3$. It also relates to certain substituted malonic acid derivative compounds, to a process for the synthesis of said substituted malonic acid derivative compounds and to the use of said substituted malonic acid derivative compounds as a synthetic intermediate in different reactions, in particular in the synthesis of Sevoflurane.

Sevoflurane is an important volatile anesthetic agent particularly suited for administration to patients during outpatient surgery. Sevoflurane is known to provide patients with a rapid rate of recovery from the anesthesia. An additional advantage of this anesthetic agent is that it can be used as an induction agent since it is not pungent and allows a rapid and smooth induction without breath holding or laryngospasm as may occur with other inhalation agents. A smooth uneventful induction is especially valuable for pediatric anesthesia where the use of intravenous induction agents can result in numerous problems and is often contraindicated.

Many of the commercial processes for the preparation of Sevoflurane make use of the chemical intermediate $CF_3$—$CH(OH)$—$CF_3$ (HFIP), as starting material. In most of these processes, unreacted HFIP may remain in the product mixture. It is known in the art that HFIP is difficult to remove from the crude Sevoflurane product.

The total manufacturing cost is mainly based on the material cost for HFIP which is expensive.

In view of the disadvantages of using HFIP, a process for recovery of HFIP from the waste stream which allows for a more efficient use of HFIP has been described in WO 2004/065340. WO 2009/085247 discloses a process for the purification of crude Sevoflurane which had been produced by reacting HFIP, formaldehyde and hydrogen fluoride (HF).

Other more complicated methods of Sevoflurane synthesis are described in U.S. Pat. No. 5,969,193 and U.S. Pat. No. 6,100,434 wherein said methods avoid this difficult Sevoflurane/HFPI separation.

It has now been found a process for the manufacture of Sevoflurane, $CF3$-$CH(OCH_2F)$—$CF_3$ which allows for improved yield, high efficiency and lower manufacturing cost in particular compared to the known processes whereby HFIP is used as chemical intermediate.

The invention consequently relates to a process for the manufacture of Sevoflurane, $CF_3$—$CH(OCH_2F)$—$CF_3$, which comprises fluorination of a substituted malonic acid derivative of formula (I) or (II):

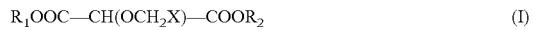

$$R_1OOC\text{—}CH(OCH_2X)\text{—}COOR_2 \quad (I)$$

$$R_3HNOC\text{—}CH(OCH_2X)\text{—}CONHR_4 \quad (II)$$

wherein

X is OH or a leaving group which can be substituted by nucleophilic substitution and which is preferably selected from halogens or oxygen containing functional groups such as OTos and OTMS.

$R_1$, $R_2$ equal to or different from each other, are independently selected from H, an alkyl group having from 1 to 10 carbon atoms which is optionally substituted by at least one halogen atom, an aralkyl group or an aryl group;

$R_3$, $R_4$ equal to or different from each other, are independently selected from H, an alkyl group having from 1 to 10 carbon atoms which is optionally substituted by at least one halogen atom, an aralkyl group or an aryl group;

For the purpose of the present invention, the term "aryl group" refers to an aromatic ring group such as phenyl and napthyl, and phenyl and napthyl substituted by at least 1 halogen atom.

For the purpose of the present invention, the term "aralkyl group" refers to an aromatic ring group substituted with alkyl groups such as tolyl, biphenylyl, etc.

Surprisingly, the process according to the invention makes it possible that the purification of Sevoflurane can be simplified, loss of material and need for disposal of by-products can be reduced and production time can be reduced.

Preferably, in the process according to the invention, $R_1$, $R_2$, $R_3$ and $R_4$ equal to or different from each other, are often independently selected from H, a C1-C4 alkyl group, optionally substituted by at least 1 halogen atom, an aryl group, for example, phenyl. More preferably, $R_1$, $R_2$, $R_3$ and $R_4$ equal to or different from each other, are independently from each other H, a linear or branched C1-C4 alkyl group optionally substituted by at least 1 halogen atom, and particularly preferably $R_1$, $R_2$, $R_3$ and $R_4$ are independently from each other H, methyl, ethyl, n-propyl or isopropyl each optionally substituted by at least 1 halogen atom, very preferably H, a methyl or an ethyl group each optionally substituted by at least 1 halogen atom. Most preferably, $R_1$, $R_2$ are H.

X is preferably selected from bromine, chlorine, iodine, OH, OTos or OTMS; more preferably X is chlorine or OH, most preferably X is chlorine or fluorine.

In a preferred aspect, $R_1$, $R_2$ are H and X is OH.

In a particularly preferred aspect, $R_1$, $R_2$ are H and X is chlorine or fluorine, and the compounds of formula (I) are HOOC—$CH(OCH_2Cl)$—COOH and HOOC—$CH(OCH_2F)$—COOH.

In another particularly preferred aspect, $R_1$ and $R_2$ are an ethyl group and X is chlorine or fluorine, and the compounds of formula (I) are EtOOC—$CH(OCH_2Cl)$—COOEt and EtOOC—$CH(OCH_2F)$—COOEt.

In general, the reaction is performed in the liquid phase.

In the process according to the invention, the fluorination is generally carried out with fluorinating agents. Said fluorinating agents preferably allow fluorinating a halogen, a hydroxyl group, a carboxyl group and other oxygen containing functional groups, in particular substituting carbon-oxygen functionality with carbon-fluorine groups. Typical examples of said fluorinating agents are for example $SF_4$ (sulfur tetrafluoride); diethylaminosulfur trifluoride (DAST), dimethylaminosulfur trifluoride (DMAST) and bis(2-methoxyethyl)aminosulfur trifluoride (Deoxofluor).

$SF_4$ is most preferred as fluorinating agent. The production of $SF_4$ can be realized according to the procedure described in the GB Pat. No. 1374054.

According to one embodiment, the fluorination with $SF_4$ is carried out in the presence of anhydrous HF. HF is often used in an amount of about 1 to about 1000 moles, and preferably about 1 to about 500 moles, per mole of $SF_4$.

In the process according to the present invention, the fluorination can be carried out in the presence of a solvent. The solvent to be used may also, for example, be an aromatic hydrocarbon such as benzene, toluene or xylene, an aliphatic hydrocarbon such as pentane or hexane; a halogenated hydrocarbon such as methylene chloride, chloroform, ethylene dichloride, hydrofluorocarbons, e.g. 1,1,1,3,3-pentafluorobutane (Solkane®365 mfc) or perfluorocarbons, e.g. perfluorocyclohexane; or an ether such as diethyl ether, dibutyl ether or tetrahydrofuran. Among them, the halogenated hydrocarbons are preferred. Methylene chloride is most preferred. These solvents may be used alone or in combination as a mixture. If appropriate, the solvent is used usually in an amount of from 50 to 99% by weight, preferably from 60 to 99% by weight, more preferably from 75 to 99% by weight of the solvent relative to the total weight of the reaction medium.

If the reaction mixture is a liquid under the reaction conditions, a solvent is not needed. If desired, starting compounds or reaction products could be used as solvent. Particularly preferred is the use of Sevoflurane as solvent. Preferably, if Sevoflurane is used as a solvent, it is present in the reaction mixture from the start.

The pressure and the temperature are selected as such that the reaction mixture remains in the liquid phase.

The process according to the present invention generally comprises carrying out the fluorination at a temperature equal to or higher than 30° C., preferably equal to or higher than 40°, more preferably equal to or higher than 50° C. It is generally carried out at a temperature equal to or lower than 90° C., preferably at a temperature equal to or lower than 80° C., more preferably a temperature equal to or lower than 70° C. A temperature ranging from 50 to 70° C. is most preferred.

The process according to the present invention generally comprises carrying out the fluorination under pressure. The pressure of the fluorination is advantageously equal to or greater than about 5 bar (abs), preferably about 10 bar (abs) to equal to or less than about 25 bar (abs).

Stoichiometrically, the transformation of 1 C(O) group to a $CF_2$ group consumes one molecule of $SF_4$. The transformation of a C—$OR_1$ or C—$OR_2$ group to a C—F group consumes half a molecule of $SF_4$, as well as the transformation of a $OCH_2X$ group to form a $OCH_2F$ group. Consequently, in the process according to the invention, the range of the molar ratio of substituted malonic acid derivative to $SF_4$ preferably is from 1:3 to 1:5, and particularly preferably from 1:3.5 to 1:4.5.

If desired, the fluorination can be carried out in 2 or even 3 steps. In the $1^{st}$ step, any hydroxyl groups are transformed. In a second step, the other groups, e.g. the carbonyl groups, are transformed. The first step often is performed at a lower temperature range, e.g. at −80° C. to 0° C. The second step is preferably performed at the temperature given above.

The invention also relates to the manufacture of a substituted malonic acid derivative of formula (I) or (II):

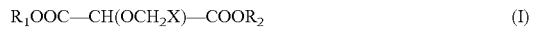  (I)

  (II)

wherein X is OH or a leaving group which can be substituted by nucleophilic substitution. The manufacture can principally be performed in two alternatives: according to one embodiment, the synthesis is performed with an O-nucleophile, and according to another embodiment, the synthesis is performed with a $CH_2$-electrophile.

Thus, according to one embodiment, the invention relates to a process for the manufacture of a substituted malonic acid derivative of formula (I) or (II):

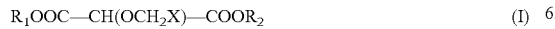  (I)

  (II)

wherein
X is OH or a leaving group which can be substituted by nucleophilic substitution. Said leaving group is preferably selected from halogens or oxygen containing functional groups such as OTos and OTMS $R_1$, $R_2$ equal to or different from each other, are independently selected from H, an alkyl group having from 1 to 10 carbon atoms which is optionally substituted by at least one halogen atom, an aralkyl group or an aryl group;

$R_3$, $R_4$ equal to or different from each other, are independently selected from H, an alkyl group having from 1 to 10 carbon atoms which is optionally substituted by at least one halogen atom, an aralkyl group or an aryl group;

by reaction of a malonic acid derivative of formula (III) or (IV):

  (III)

  (IV)

wherein
Y is a leaving group which can be substituted by nucleophilic substitution. Y is preferably selected from halogens or oxygen containing functional groups such as OTos and OTMS, $R_1$, $R_2$, $R_3$ and $R_4$ are as defined above, with an O-nucleophile.

The definitions and preferences described above for the process for the manufacture of Sevoflurane according to the invention equally apply to the process for the manufacture of said substituted malonic acid derivative.

Typical examples of O-nucleophiles are formaldehyde and formaldehyde derivatives.

Formaldehyde and formaldehyde derivatives are preferred O-nucleophiles.

For the purpose of the present invention, the term "formaldehyde derivative" refers to a class of molecules which are formed from formaldehyde by polymerization, trimerisation or addition reactions such as paraformaldehyde, trioxane, hydrated formaldehyde, hemiacetalic structures of formaldehyde of formula (V): HO—$CH_2$—X wherein X is a leaving group which can be substituted by nucleophilic substitution and which is preferably selected from halogens or oxygen containing functional groups. Typical examples of said hemiacetalic compounds are for instance HO—$CH_2$—OTos and HO—$CH_2$OTMS.

In general, the paraformaldehyde or trioxane is cracked, e.g. thermally or chemically, to form the monomeric formaldehyde.

The process according to the present invention generally comprises carrying out the reaction with the O-nucleophile in the presence of a solvent. The solvent to be used may, for example, be a polar solvent such as dimethyl formamide, dimethyl acetamide, dimethylsulfoxide, sulfolane, Sevoflurane, tetrahydrofuran, acetonitrile, dioxane, a halogenated hydrocarbon such as methylene chloride, chloroform or ethylene dichloride; or an ether such as diethyl ether, dibutyl ether or tetrahydrofuran. Among them, a polar solvent is preferred. Particularly preferred among them, is dimethyl formamide, sulfolane or Sevoflurane. These solvents may be used alone or in combination as a mixture. If appropriate, the solvent is used usually in an amount of from 50 to 99 by weight, preferably from 60 to 99% by weight, more preferably from 75 to 99% by weight of the solvent relative to the total weight of the reaction medium.

If desired, the reaction with the O-nucleophile optionally may be carried out in the presence of a base. If a base is used, it may be an inorganic base or an organic base. The inorganic base may be selected from the group consisting of alkali metal hydroxides such as sodium hydroxide, potassium hydroxide, lithium hydroxide, cesium hydroxide, alkaline earth metal hydroxides such as calcium hydroxide, barium hydroxide, magnesium hydroxide, strontium hydroxide, and basic alkali metal salts such as sodium carbonate, sodium hydrogencarbonate, potassium carbonate and potassium hydrogencarbonate. Preferred bases are sodium hydroxide and potassium hydroxide. Most preferred base is sodium hydroxide. The organic base may be selected from the group consisting of nitrogen-containing heterocyclic compounds such as pyridine, quinoline or picoline; and tertiary bases such as triethylamine, dimethylaniline, diethylaniline and 4-dimethylaminopyridine. Among them, pyridine, triethylamine, dimethylaniline, diethylaniline and 4-dimethylaminopyridine are preferred. Among them, pyridine is particularly preferred. These bases may be used alone or in combination as a mixture.

If desired, the base can be applied in the form of an aqueous solution or a solution of the base in water and an organic solvent. The organic solvent is in particular a solvent as described above.

For the purpose of the present invention, the term "aqueous solution" refers to solutions of water soluble compounds in water, for example salt water or any other aqueous mineral salt solution.

In the process according to the invention, the molar ratio of the base to O-nucleophile is advantageously from 0.5:1 to 2:1, preferably from 0.7:1 to 1.5:1, and more preferably from 0.8:1 to 1.2:1. Most preferably, the molar ratio is about 1.

According to the other embodiment, the present invention concerns a process for the manufacture of a hydroxyl substituted malonic acid derivative of formula (VI) or (VII):

R$_1$OOC—CH(OCH$_2$OH)—COOR$_2$ (VI)

R$_3$HNOC—CH(OCH$_2$X)—CONHR$_4$ (VII)

wherein R$_1$, R$_2$ R$_3$ and R$_4$ equal to or different from each other, are independently selected from H, an alkyl group having from 1 to 10 carbon atoms optionally substituted by at least one halogen atom, an aralkyl group or an aryl group, comprising the reaction of a hydroxyl malonic acid derivative of formula (VIII) or (IX): R$_1$OOC—CH(OH)—COOR$_2$ (VIII) or R$_3$HNOC—CH(OH)—CONHR$_4$ (IX) wherein R$_1$, R$_2$ R$_3$ and R$_4$ are as defined above, with a CH$_2$-electrophile.

Formaldehyde is most preferred CH$_2$-electrophile.

Optionally, the hydroxyl malonic acid derivative of formula (VI) or (VII): R$_1$OOC—CH(OCH$_2$OH)—COOR$_2$ (VI) or R$_3$HNOC—CH(OCH$_2$OH)—CONHR$_4$ (VII) can be converted to the substituted malonic acid derivative of formula (I) or (II):

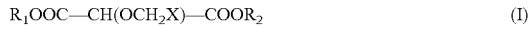
R$_1$OOC—CH(OCH$_2$X)—COOR$_2$ (I)

R$_3$HNOC—CH(OCH$_2$X)—CONHR$_4$ (II)

wherein X is in particular a leaving group, as described above. The conversion can be realized by reaction of said hydroxyl substituted malonic acid derivative with PCl$_3$, PCl$_5$, TosOH, MesOH or amine.nHCl like Py.HCl.

According to the most preferred embodiment, the present invention concerns a process for the manufacture of a substituted malonic acid derivative of formula (I) or (II):

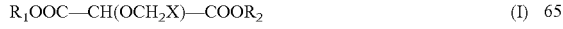
R$_1$OOC—CH(OCH$_2$X)—COOR$_2$ (I)

R$_3$HNOC—CH(OCH$_2$X)—CONHR$_4$ (II)

wherein
X is a leaving group which can be substituted by nucleophilic substitution. Said leaving group is preferably selected from halogens or oxygen containing functional groups such as OTos and OTMS
R$_1$, R$_2$ equal to or different from each other, are independently selected from H, an alkyl group having from 1 to 10 carbon atoms which is optionally substituted by at least one halogen atom, an aralkyl group or an aryl group;
R$_3$, R$_4$ equal to or different from each other, are independently selected from H, an alkyl group having from 1 to 10 carbon atoms which is optionally substituted by at least one halogen atom, an aralkyl group or an aryl group;
comprising the reaction of a hydroxyl malonic acid derivative of formula (VIII) or (IX): R$_1$OOC—CH(OH)—COOR$_2$ (VIII) or R$_3$HNOC—CH(OH)—CONHR$_4$ (IX) wherein R$_1$, R$_2$ R$_3$ and R$_4$ are as defined above, with a CH$_2$-electrophile in the presence of a leaving group transfer agent.

For the purpose of the present invention, the term "leaving group transfer agent" refers to a class of compounds that are able to transfer their leaving group to another compound. Typical examples of leaving group transfer agents are for example a chlorinating agent selected from the group consisting of oxalyl chloride, phosphorus trichloride, phosphorus pentachloride or phosphorus oxychloride, a thionyl compound such as thionyl chloride and thionyl fluoride; a sulfuryl compound such as sulfuryl chloride and sulfuryl fluoride; a tosylating agent such as p-toluenesulfonyl chloride (tosyl chloride) and p-toluenesulfonyl fluoride (tosyl fluoride), or a mesylating agent, such as methanesulfonyl chloride (mesyl chloride) and methanesulfonyl fluoride (mesyl fluoride).

Preferred leaving group transfer agents are thionyl and sulfuryl compounds. Most preferred leaving group transfer agents are thionyl compounds. Preferred thionyl compounds are thionyl chloride and thionyl fluoride.

In a particular aspect of this embodiment, the reaction of the hydroxyl malonic acid derivative of formula (VIII) or (IX): R$_1$OOC—CH(OH)—COOR$_2$ (VIII) or R$_3$HNOC—CH(OH)—CONHR$_4$ (IX) wherein R$_1$, R$_2$ R$_3$ and R$_4$ are as defined above, with a CH$_2$-electrophile in the presence of a leaving group transfer agent may be carried out additionally in the presence of a strong acid. The strong acid may be selected for example from the group consisting of fuming sulfuric acid, fuming nitric acid and hydrogen halides such as in particular hydrogen chloride, hydrogen fluoride.

In a first specific embodiment, the strong acid is a fuming sulfuric acid.

In a second specific embodiment, the strong acid is hydrogen chloride or hydrogen fluoride.

In a preferred aspect, R$_1$, R$_2$ are H and X is chlorine or fluorine, and the compounds of formula (I) are HOOC—CH(OCH$_2$Cl)—COOH and HOOC—CH(OCH$_2$F)—COOH.

The invention also relates to a process for the manufacture of Sevoflurane CF$_3$—CH(OCH$_2$F)—CF$_3$ which comprises the steps of (a) manufacturing a substituted malonic acid derivative of formula (I) or (II):

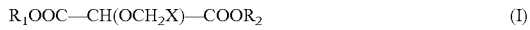
R$_1$OOC—CH(OCH$_2$X)—COOR$_2$ (I)

R$_3$HNOC—CH(OCH$_2$X)—CONHR$_4$ (II)

wherein
X is OH or a leaving group which can be substituted by nucleophilic substitution. Said leaving group is preferably selected from halogens or oxygen containing functional groups such as OTos and OTMS.

$R_1$, $R_2$ equal to or different from each other, are independently selected from H, an alkyl group having from 1 to 10 carbon atoms which is optionally substituted by at least one halogen atom, an aralkyl group or an aryl group;

$R_3$, $R_4$ equal to or different from each other, are independently selected from H, an alkyl group having from 1 to 10 carbon atoms which is optionally substituted by at least one halogen atom, an aralkyl group or an aryl group;

according to the process according to the invention as described above, and (b) further reacting said malonic acid derivative as intermediate for the manufacture of Sevoflurane $CF_3$—CH($OCH_2F$)—$CF_3$ under the reaction conditions according to the process according to the invention, as described above.

In a preferred embodiment of this process of the present invention, the manufacture of Sevoflurane $CF_3$—CH($OCH_2F$)—$CF_3$ comprises the steps of (a) manufacturing a substituted malonic acid derivative of formula (I) or (II):

  (I)

  (II)

wherein

X is a leaving group which can be substituted by nucleophilic substitution. Said leaving group is selected from halogens, in particular chlorine $R_1$, $R_2$ equal to or different from each other, are independently selected from H, an alkyl group having from 1 to 10 carbon atoms which is optionally substituted by at least one halogen atom, an aralkyl group or an aryl group;

$R_3$, $R_4$ equal to or different from each other, are independently selected from H, an alkyl group having from 1 to 10 carbon atoms which is optionally substituted by at least one halogen atom, an aralkyl group or an aryl group;

according to the most preferred embodiment of the process according to the invention as described above, and (c) further reacting said malonic acid derivative as intermediate for the manufacture of Sevoflurane $CF_3$—CH($OCH_2F$)—$CF_3$ under the reaction conditions according to the process according to the invention, as described above.

In a particularly preferred aspect, $R_1$, $R_2$ are H and X is chlorine or fluorine, and the compounds of formula (I) are HOOC—CH($OCH_2Cl$)—COOH and HOOC—CH($OCH_2F$)—COOH.

In another particularly preferred aspect, $R_1$, $R_2$ are an ethyl group and X is chlorine or fluorine, and the compounds of formula (I) are EtOOC—CH($OCH_2Cl$)—COOEt and EtOOC—CH($OCH_2F$)—COOEt.

The processes according to the invention for the manufacture of the intermediate substituted malonic acid derivative and for the reaction of said intermediate to form Sevoflurane and the particular embodiments thereof can be carried out batchwise or continuously.

Said processes according to the invention and the particular embodiments thereof can be performed in any suitable reactor, e.g. in an autoclave.

In a specific embodiment, the process according to the invention further comprises separating Sevoflurane from the reaction mixture which is obtained in accordance with any of the processes disclosed herein before or a combination thereof, by known methods, e.g. by distillation, precipitation and/or crystallization.

A distillation, in particular a fractional distillation, is preferred as separation technique to separate the Sevoflurane from the reaction mixture from hydrogen fluoride, from unreacted reactants such as the malonic acid derivative and the substituted derivative thereof and unreacted hemiacetalic compounds, from by products such as $SOF_2$, alcoholic compounds or alkyl halide by-products. Typical examples are for instance EtOH or EtCl. The by products may eliminate $H_2O$ or HCl and may be separated out of the liquid mixtures as ethylene.

The invention also relates to a substituted malonic acid derivative of formula (I) or (II):

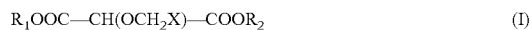  (I)

  (II)

wherein

X is OH or a leaving group which can be substituted by nucleophilic substitution and which is preferably selected from halogens or oxygen containing functional groups such as OTos and OTMS.

$R_1$, $R_2$ equal to or different from each other, are independently selected from H, an alkyl group having from 1 to 10 carbon atoms which is optionally substituted by at least one halogen atom, an aralkyl group or an aryl group;

$R_3$, $R_4$ equal to or different from each other, are independently selected from H, an alkyl group having from 1 to 10 carbon atoms which is optionally substituted by at least one halogen atom, an aralkyl group or an aryl group;

The definitions and preferences described above for the process for the manufacture of the substituted malonic acid derivative according to the invention equally apply here.

Preferred substituted malonic acid derivatives are HOOC—CH($OCH_2Cl$)—COOH and HOOC—CH($OCH_2F$)—COOH.

The invention also relates to the use of a substituted malonic acid derivative of formula (I) or (II):

  (I)

  (II)

wherein

X is OH or a leaving group which can be substituted by nucleophilic substitution and which is preferably selected from halogens or oxygen containing functional groups such as OTos and OTMS.

$R_1$, $R_2$ equal to or different from each other, are independently selected from H, an alkyl group having from 1 to 10 carbon atoms which is optionally substituted by at least one halogen atom, an aralkyl group or an aryl group;

$R_3$, $R_4$ equal to or different from each other, are independently selected from H, an alkyl group having from 1 to 10 carbon atoms which is optionally substituted by at least one halogen atom, an aralkyl group or an aryl group;

as an intermediate for the manufacture of Sevoflurane. Preferably, HOOC—CH($OCH_2Cl$)—COOH or HOOC—CH($OCH_2F$)—COOH is used.

Thus, the invention provides a process for the manufacture of Sevoflurane wherein a substituted malonic acid derivative of formula (I) or (II):

$$R_1OOC-CH(OCH_2X)-COOR_2 \quad (I)$$

$$R_3HNOC-CH(OCH_2X)-CONHR_4 \quad (II)$$

wherein $R_1$, $R_2$, $R_3$ and $R_4$ and X have the meanings given above, is used as starting material.

Preferably, in the process according to the invention, $R_1$, $R_2$, $R_3$, $R_4$ equal to or different from each other, are often independently selected from H, a C1-C4 alkyl group, optionally substituted by at least 1 halogen atom, an aryl group, for example, phenyl. More preferably, $R_1$, $R_2$, $R_3$ and $R_4$ equal to or different from each other, are independently from each other H, a linear or branched C1-C4 alkyl group optionally substituted by at least 1 halogen atom, and particularly preferably $R_1$, $R_2$, $R_3$ and $R_4$ are independently from each other H, methyl, ethyl, n-propyl or isopropyl each optionally substituted by at least 1 halogen atom, very preferably H, a methyl or an ethyl group each optionally substituted by at least 1 halogen atom. Most preferably, $R_1$, $R_2$ are H.

X is preferably selected from bromine, chlorine, iodine, OH, OTos or OTMS; more preferably X is chlorine or OH.

In a preferred aspect, $R_1$, $R_2$ are H and X is OH.

In another preferred aspect, $R_1$, $R_2$ are H and X is chlorine or fluorine, and the compounds of formula (I) are HOOC—CH(OCH$_2$Cl)—COOH and HOOC—CH(OCH$_2$F)—COOH.

The examples here after are intended to illustrate the invention without however limiting it.

EXAMPLE 1

General Procedure for the Preparation of the Compound of Formula (I): EtOOC—CH(OCH$_2$Cl)—COOEt Procedure A: Into an ice-cooled suspension of paraformaldehyde (1.82 g; 1.2 eq.) and diethyl 2-hydroxymalonate (10 g; 1 eq.), 5.7 ml (1.75 eq.) thionyl chloride and subsequently, 3.6 ml (1.6 eq.) concentrated sulfuric acid were added dropwise. After 3 hours, the reaction mixture was added to ice and neutralized with NaHCO$_3$. The extraction was performed with diethyl ether, and the resulting solution was dried with Na$_2$SO$_4$. After removal of the solvent, about 8 g of the raw product were obtained.

Procedure B: Procedure A was repeated but using instead Solkane® 365 mfc for performing the extraction. Comparable results were obtained.

Table 1 shows the influence of different parameters; e.g. purity of the diethyl 2-hydroxymalonate on the selectivity of the reaction, using procedure A.

| Diethyl-2-hydroxy-malonate Purity | Diethyl-2-hydroxy-malonate Eq. amount | Para form-aldehyde Eq. amount | Thionyl chloride Eq. amount | H$_2$SO$_4$ Eq. amount | Selectivity in GC-% Compound (I) |
|---|---|---|---|---|---|
| 100% concentration | 1 eq. | 1.2 eq. | 1.75 eq. | 1.6 eq. | 98% |
|  | 1 eq. | 1.3 eq. | 2.5 eq. | 2.6 eq. | 97% |
|  | 1 eq. | 1.2 eq. | 1.75 eq. | 1.6 eq. | 99% |
| 99.4% concentration | 1 eq. | 1.2 eq. (trioxane) | 1.75 eq. | 1.6 eq. | 95.5% |
| 95% concentration | 1 eq. | 1.2 eq. | 1.75 eq. | 1.6 eq. | 81.5% |
|  | 1 eq. | 1.2 eq. | 1.75 eq. | 1.6 eq. | 94.6% |
|  | 1 eq. | 1.2 eq. | 2.2 eq. | 1.8 eq. | 83% |
|  | 1 eq. | 1.2 eq. | 1.6 eq. | 1.6 eq. | 65% |
|  | 1 eq. | 1.5 eq. | 1.75 eq. | 1.6 eq. | 70% |
|  | 1 eq. | 1.2 eq. | 2 eq. | 1.6 eq. | 45.5% |
|  | 1 eq. | 1 eq. | 1.75 eq. | 1.6 eq. | 74% |
|  | 1 eq. | 0.9 eq. | 1.75 eq. | 1.6 eq. | 74% |

EXAMPLE 2

Manufacture of Sevoflurane 10.0 g (0.045 mol) EtOOC—CH(OCH$_2$Cl)—COOEt obtained according to the procedure in example 1 is dissolved in 12.5 g (0.08 mol) Solkane® 365 mfc, 1.6 g (0.08 mol) HF, 21.8 g (0.202 mol) of SF$_4$ gas is introduced into the liquid medium in an Roth autoclave (high grade stainless steel 1.4571). The temperature is increased from 23° C. to 28° C. while introducing the SF$_4$. The autoclave is heated to 100° C. over night reaching a final pressure of 60 bar. After cooling down the autoclave content is expanded and poured out into ice water. The GC analysis of the organic phase shows the presence of Sevoflurane.

EXAMPLES 3a AND 3b

Manufacture of Sevoflurane

Example 2 is repeated but using instead a liquid medium containing HOOC—CH(OCH$_2$OH)—COOH (example 3a) or HOOC—CH(OCH$_2$Cl)—COOH (example 3b) dissolved in Solkane® 365 mfc. The GC analysis shows for both examples 3a and 3b that the product gases contain Sevoflurane.

The invention claimed is:

1. A process for the manufacture of Sevoflurane (CF$_3$—CH(OCH$_2$F)—CF$_3$) which comprises fluorination of a substituted malonic acid derivative of formula (I) or (II):

$$R_1OOC-CH(OCH_2X)-COOR_2 \quad (I)$$

$$R_3HNOC-CH(OCH_2X)-CONHR_4 \quad (II)$$

wherein
X is OH or a leaving group which can be substituted by nucleophilic substitution;
$R_1$, $R_2$, equal to or different from each other, are independently selected from the group consisting of H, an alkyl group having from 1 to 10 carbon atoms which is optionally substituted by at least one halogen atom, an aralkyl group, and an aryl group; and
$R_3$, $R_4$, equal to or different from each other, are independently selected from the group consisting of H, an alkyl group having from 1 to 10 carbon atoms which is optionally substituted by at least one halogen atom, an aralkyl group, and an aryl group.

2. The process according to claim 1, wherein $R_1$, $R_2$ are H.

3. The process according to claim 1, wherein X is chlorine, fluorine or OH.

4. The process according to claim 3, wherein X is chlorine or fluorine, and wherein $R_1$, $R_2$ are H.

5. The process according to claim 3, wherein $R_1$, $R_2$ are H, and wherein X is OH.

6. The process according to claim 1, wherein $R_1$ and $R_2$ are an ethyl group, and wherein X is chlorine or fluorine.

7. The process according to claim 1, wherein the fluorination is carried out with a fluorinating agent which is SF$_4$.

8. The process according to claim 7, wherein the range of the molar ratio of substituted malonic acid derivative to SF$_4$ is from 1:3.5 to 1:4.5.

9. The process according to claim 1, wherein the fluorination is carried out at a temperature in the range from 50 to 70° C.

10. The process according to claim 1, wherein the pressure of the fluorination is from 5 bar to 25 bar.

11. A process for the manufacture of Sevoflurane $CF_3$—$CH(OCH_2F)$—$CF_3$ which comprises the steps of
(a) carrying out the process for the manufacture of a substituted malonic acid derivative of formula (I) or (II):

$$R_1OOC-CH(OCH_2X)-COOR_2 \quad (I)$$

$$R_3HNOC-CH(OCH_2X)-CONHR_4 \quad (II)$$

wherein
X is OH or a leaving group which can be substituted by nucleophilic substitution;
$R_1$, $R_2$, equal to or different from each other, are independently selected from the group consisting of H, an alkyl group having from 1 to 10 carbon atoms which is optionally substituted by at least one halogen atom, an aralkyl group, and an aryl group; and
$R_3$, $R_4$, equal to or different from each other, are independently selected from the group consisting of H, an alkyl group having from 1 to 10 carbon atoms which is optionally substituted by at least one halogen atom, an aralkyl group, and an aryl group;
wherein the process for the manufacture of a substituted malonic acid derivative of formula (I) or (II) comprises reaction of a malonic acid derivative of formula (III) or (IV) with an O-nucleophile, $$R_1OOC-CH(Y)-COOR_2 \quad (III)$$

$$R_3HNOC-CH(Y)-CONHR_4 \quad (IV)$$

wherein
Y is a leaving group which can be substituted by nucleophilic substitution; and
$R_1$, $R_2$ in formula (III) are the same as in formula (I); and
$R_3$, $R_4$ in formula (IV) are the same as in formula (II); and
(b) further fluorinating said substituted malonic acid derivative of formula (I) or (II) for the manufacture of Sevoflurane $CF3$-$CH(OCH_2F)$—$CF_3$.

12. A process for the manufacture of Sevoflurane $CF_3$—$CH(OCH_2F)$—$CF_3$ which comprises the steps of
(a) carrying out the process for the manufacture of a substituted malonic acid derivative of formula (I) or (II):

$$R_1OOC-CH(OCH_2X)-COOR_2 \quad (I)$$

$$R_3HNOC-CH(OCH_2X)-CONHR_4 \quad (II)$$

wherein
X is OH or a leaving group which can be substituted by nucleophilic substitution;
$R_1$, $R_2$, equal to or different from each other, are independently selected from the group consisting of H, an alkyl group having from 1 to 10 carbon atoms which is optionally substituted by at least one halogen atom, an aralkyl group, and an aryl group;
$R_3$, $R_4$, equal to or different from each other, are independently selected from the group consisting of H, an alkyl group having from 1 to 10 carbon atoms which is optionally substituted by at least one halogen atom, an aralkyl group, and an aryl group;
wherein the process for the manufacture of a substituted malonic acid derivative of formula (I) or (II) comprises the reaction of a hydroxyl malonic acid derivative of formula (VIII) or (IX):

$$R_1OOC-CH(OH)-COOR_2 \quad (VIII) \text{ or}$$

$$R_3HNOC-CH(OH)-CONHR_4 \quad (IX)$$

with a $CH_2$-electrophile,
wherein
$R_1$, $R_2$ in formula (VIII) are the same as in formula (I); and
$R_1$, $R_2$ in formula (IX) are the same as in formula (II);
and
(b) further fluorinating said substituted malonic acid derivative of formula (I) or (II) for the manufacture of Sevoflurane $CF_3$—$CH(OCH_2F)$—$CF_3$.

13. The process of claim 1 wherein X is OH or a leaving group which can be substituted by nucleophilic substitution and which is selected from the group consisting of halogens and oxygen containing functional groups.

14. The process of claim 11 wherein Y is a leaving group which can be substituted by nucleophilic substitution, and wherein Y is selected from the group consisting of halogens and oxygen containing functional groups.

15. The process of claim 14 wherein the oxygen containing functional groups are selected from the group consisting of OTos and OTMS.

16. The process of claim 12 wherein step (a) is carried out in the presence of a leaving group transfer agent and X is a leaving group which can be substituted by nucleophilic substitution, and wherein said leaving group is selected from the group consisting of halogens and oxygen containing functional groups.

17. The process of claim 16 wherein the oxygen containing functional groups are selected from the group consisting of OTos and OTMS.

18. The process of claim 11 wherein X is OH or a leaving group which can be substituted by nucleophilic substitution and which is selected from the group consisting of halogens and oxygen containing functional groups.

19. The process of claim 12 wherein X is a leaving group which can be substituted by nucleophilic substitution, and wherein said leaving group is selected from the group consisting of chlorine and fluorine.

20. The process according to claim 12, wherein X is OH.

21. The process according to claim 11, wherein the O-nucleophile is formaldehyde or a formaldehyde derivative.

22. The process according to claim 11, wherein step (a) is carried out in the presence of a base.

23. The process according to claim 12, wherein the $CH_2$-electrophile is formaldehyde.

24. The process according to claim 12, wherein the leaving group transfer agent is a thionyl compound.

\* \* \* \* \*